United States Patent
Wu et al.

(10) Patent No.: US 7,060,825 B2
(45) Date of Patent: Jun. 13, 2006

(54) PROCESS FOR SYNTHESIZING 6-QUINAZOLINYL-ETHYL-BENZOYL AND RELATED ANTIFOLATES

(75) Inventors: Ye Wu, Helotes, TX (US); Harry Kochat, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 10/627,483

(22) Filed: Jul. 25, 2003

(65) Prior Publication Data

US 2005/0020833 A1     Jan. 27, 2005

(51) Int. Cl.
*C07D 239/80*     (2006.01)
*C07D 239/84*     (2006.01)

(52) U.S. Cl. ..................... 544/285; 544/286; 544/287; 544/291; 544/292; 544/293

(58) Field of Classification Search ................ 544/285, 544/286, 287, 291, 292, 293, 283
See application file for complete search history.

(56) References Cited

U.S. PATENT DOCUMENTS 5,912,251 A * 6/1999 Nair .................. 514/266.4

OTHER PUBLICATIONS

Yan, S. J.; Weinstock, Louis T.; Cheng, C. C., Journal of Heterocyclic Chemistry, 16(3), 541-4 1979.*
Oatis, John E., Jr.; Hynes, John B. Journal of Medicinal Chemistry, 20(11), 1393-6 (English) 1977.*
Harris, Neil V.; Smith, Christopher; Bowden, Keith, Eur. J. Med. Chem., 27, 7-18, 1992.*
Vaidya, Chitra M.; Wright, Joel E.; Rosowsky, Andre,Journal of Medicinal Chemistry, 45(8), 1690-1696, 2002.*
Acharya, J.B. et al, J. Heterocyclic Chem., 12, 1975, 1283-1286.*
House, Herbert O., Modern Synthetic Reactions, Second edition, 1972, W.A. Benjamin, Menlo Park, CA, p. 690.*
Name Reactions, Organic Chemistry Portal [retrieved on Jan. 13, 2006 ]. Retrieved from the Internet <http://www.organic-chemistry.org/frames.htm?http://www.organic-chemistry.org/namedreactions/wittig-horner-reaction.shtm>.*
Jerry March, "Advanced Organic Chemistry—Reactions, Mechanisms, and Structure," Fourth Edition, John Wiley & Sons (1992).

* cited by examiner

*Primary Examiner*—Thomas C. McKenzie
(74) *Attorney, Agent, or Firm*—Akin Gump Strauss Hauer & Feld, LLP

(57) ABSTRACT

The invention claimed herein relates to an improvement in a process for synthesizing a compound of formula Ib:

wherein $R_1$ and $R_2$ are each individually amino or N-alkyl substituted amino; hydroxy; alkoxy; keto; lower alkyl; or a nitrogen or oxygen protecting group;
$R_3$ is hydrogen; hydroxy; alkoxy; trifluoromethyl alkoxy; halo; sulfhydryl or alkylthio;
$R_4$ is —C(O)—X;
X is hydroxy; alkoxy; or an amino acid residue;
in which process a 2-amino-5-nitro-benzonitrile starting reagent is cyclized to form 2,4-diamino-6-nitro-quinazoline, which is converted to 2,4,6-triamino-quinazoline, which is converted to 2,4-diamino-6-cyano-quinazoline, which is converted to 2,4-diamino-6-formyl-quinazoline;
in which the improvement includes:
reacting an $R_4$-p-benzoic acid alkylene moiety with triethyl phosphite to form a 4-$R_4$-carbonyloxyalkyl-phenyl-alkyldiethylphosphite; and
reacting the 2,4-diamino-6-formyl-quinazoline with the 4-$R_4$-carbonyloxyalkyl-phenyl-alkyldiethylphosphite to form the compound of formula Ib.

(Ib)

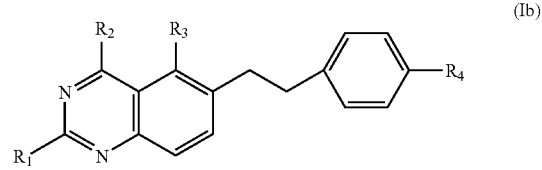

7 Claims, No Drawings

PROCESS FOR SYNTHESIZING 6-QUINAZOLINYL-ETHYL-BENZOYL AND RELATED ANTIFOLATES

FIELD OF THE INVENTION

This invention relates to novel and useful processes for synthesizing compounds that are analogues of γ-methylene-10-deazaaminopterin (MDAM), and will have application to the synthesis of certain di- and tri-deaza analogues thereof.

BACKGROUND OF THE INVENTION

Antifolates comprise a well-known class of compounds that have exhibited beneficial medicinal properties in several therapeutic areas. Antifolates have been used for many years as treatments for various cancers, infectious diseases, immunosuppression, inflammatory diseases and others.

Antifolates are so named because of their mode of action, by interfering with the folic acid metabolic pathway. The most well known antifolate, methotrexate (MTX), inhibits dihydrofolate reductase (DHFR), thus preventing the reduction of folic acid to its dihydro and tetrahydro forms. Other antifolates, such as aminopterin (AMT), MDAM and others also act by inhibiting DHFR, while still others, such as MTX polyglutamates, act at different areas of the folic acid pathway, most notably the thymidylate synthetase (TS) inhibitors, Glucineamide Ribonucleotide (GAR) and Aminoimidazole Carboxamide Ribonucleotide (AICAR) inhibition.

Most antifolates used in oncology are similar in chemical structure to the naturally occurring vitamin, folic acid, the structure of which is shown below, along with a few other widely known antifolate structures.

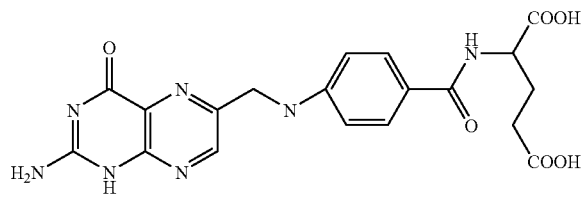
Folic Acid

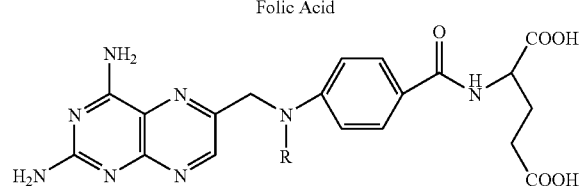
MTX-R = methyl
AMT-R = hydrogen

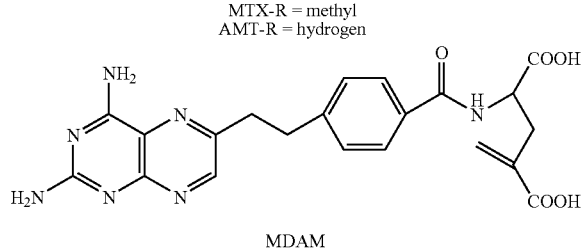
MDAM

U.S. Pat. No. 5,912,251 discloses an antifolate compound, hereinafter referred to as 5,8-dideaza MDAM that is similar in structure to MDAM. The structure of 5,8-dideaza MDAM (hereinafter referred to as gamma methylene glutamate 5,8,10-trideaza aminopterin or TRIDAM) is shown below as Formula A.

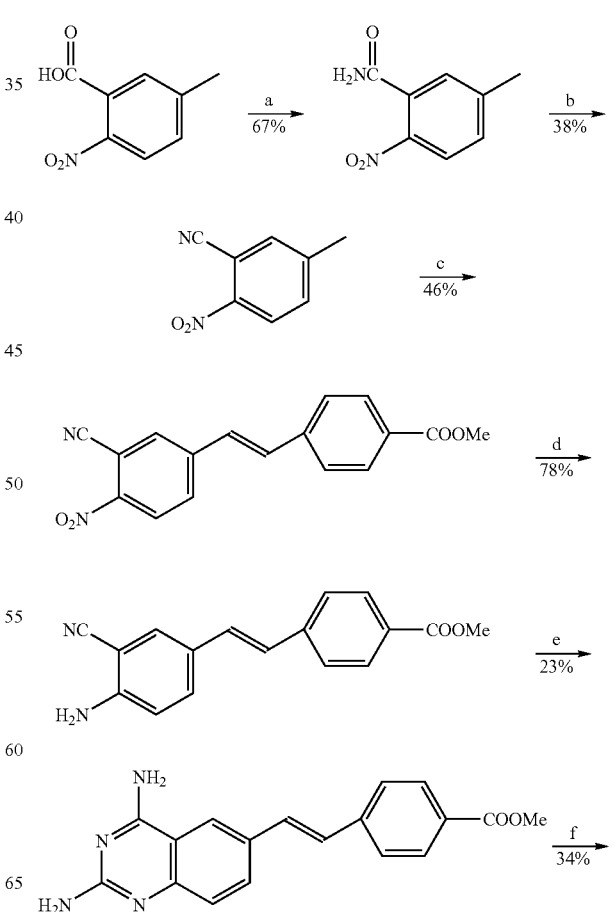

A major mode of action of TRIDAM is TS inhibition in addition to some degree of DHFR inhibition. It has been postulated in the '251 patent that TRIDAM may find application not only in oncology, but also in other medical areas that antifolates have found success. Asthma, rheumatoid arthritis, psoriasis, and other inflammatory diseases are potential targets for TRIDAM.

The previous process for synthesizing TRIDAM and analogues thereof, as disclosed in the '251 patent, is inefficient and not commercially viable due to low overall yields and the impractical application or costs of various reagents and procedures used; the overall yield from the process is less than one percent of the starting materials. The '251 process is depicted below as Scheme A.

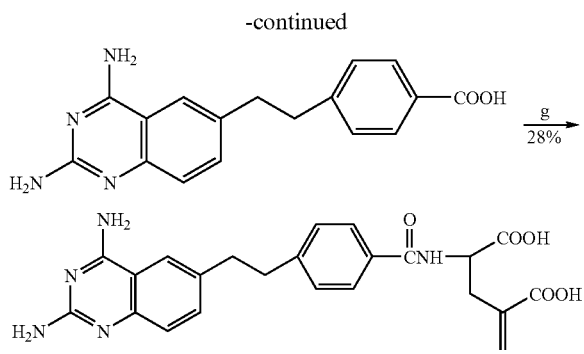

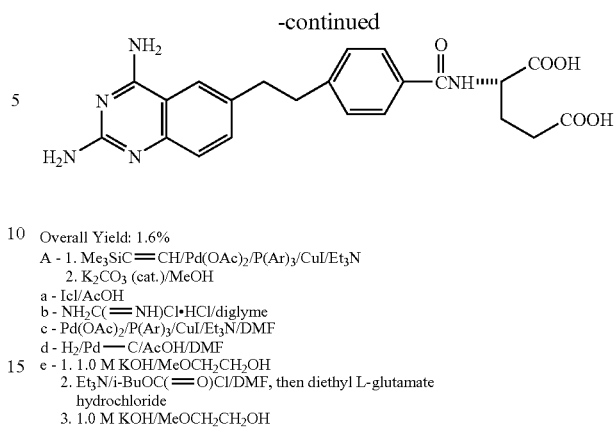

Overall Yield: 1.6%
A - 1. Me₃SiC≡CH/Pd(OAc)₂/P(Ar)₃/CuI/Et₃N
    2. K₂CO₃ (cat.)/MeOH
a - ICl/AcOH
b - NH₂C(=NH)Cl•HCl/diglyme
c - Pd(OAc)₂/P(Ar)₃/CuI/Et₃N/DMF
d - H₂/Pd—C/AcOH/DMF
e - 1. 1.0 M KOH/MeOCH₂CH₂OH
    2. Et₃N/i-BuOC(=O)Cl/DMF, then diethyl L-glutamate hydrochloride
    3. 1.0 M KOH/MeOCH₂CH₂OH N. V. Harris. et al., *Synlett.*, No. 4, 577 (1990).

SUMMARY OF THE INVENTION

The process of this invention provides for an efficient and economical process for synthesizing TRIDAM and intermediates thereof, together with certain analogues, derivatives and/or congeners thereof.

The critical intermediate synthesized according to the process of this invention is the analogue of pteroic acid, shown below as Formula I.

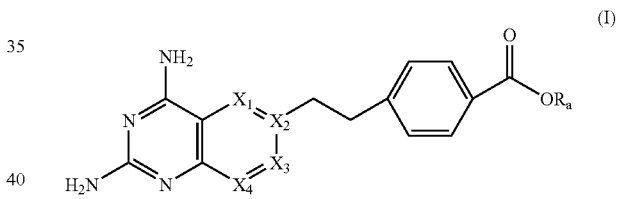

where $R_a$ is hydrogen, lower alkyl, or any oxygen protecting group, and $X_2$ is carbon or nitrogen, and $X_1$, $X_3$ and $X_4$ are each individually CH or nitrogen.

Once intermediate I has been synthesized, known methods may be utilized to couple an amino acid residue to the molecule to form the desired antifolate compound. Preferred amino acids are glutamic acid, aspartic acid and their derivatives, most preferably the naturally occurring L-enantiomer, but other amino acids may also be employed.

An object of this invention is to provide for an efficient and economical process for synthesizing antifolate compounds.

DESCRIPTION OF THE PREFERRED EMBODIMENT

The preferred embodiment herein described is not intended to be exhaustive or to limit the invention to the precise form disclosed. It is chosen and described to explain the principles of the invention, and its application and practical use to enable others skilled in the art to follow its teachings.

The process of this invention provides for the synthesis of compounds having the formula Ia below:

Overall Yield: 0.20%
a - i-BuOC(=O)Cl, Et₃N, NH₃, DCM
b - POCl₃, DMF
c - Methyl 4-formylbenzoate, NaOMe, MeOH
d - Na₂S₂O₄, DMF
e - Guanidine
f - 1. H₂/Pd—C, DMF 2. 0.1N NaOH
g - 1. Et₃N/i-BuOC(=O)Cl/DMF
    2. diethyl L-glutamate hydrochloride
    3. 0.1N NaOH M. G. Nair, U.S. Pat. No. 5,912,251 (1999). Another reported synthetic process for making a close analogue of TRIDAM (identical in all respects except for the amino acid residue) was disclosed by N. V. Harris, et, al., *Synlett.*, No. 4,577 (1990), and is shown below as Scheme B.

SCHEME B

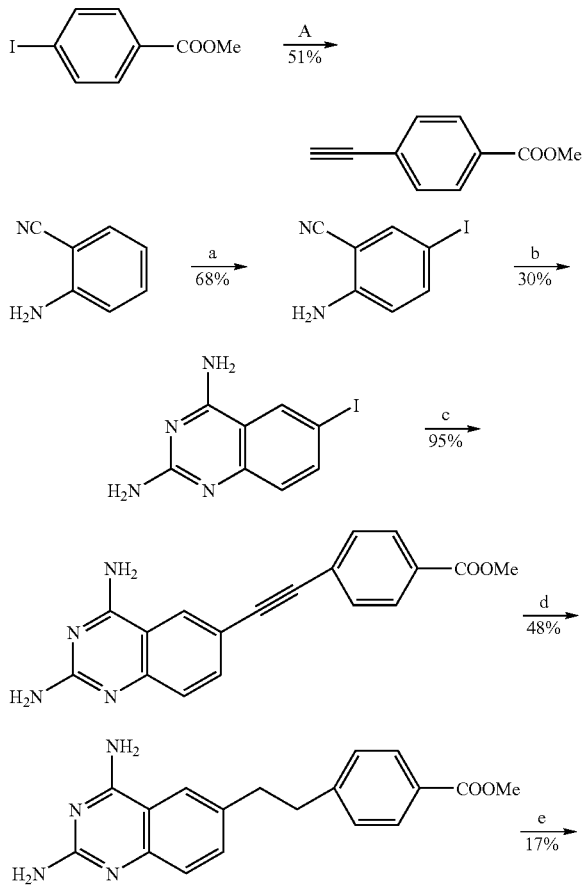

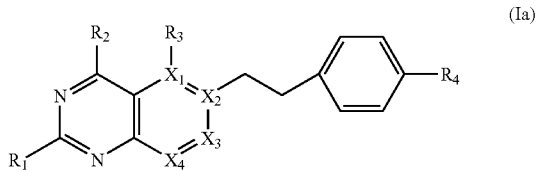

(Ia)

wherein $R_1$ and $R_2$ are each individually amino or N-alkyl substituted amino; hydroxy; alkoxy; keto; lower alkyl; or a nitrogen or oxygen protecting group;

$R_3$ is hydrogen; hydroxy; alkoxy; trifluoromethyl alkoxy; halo; sulfhydryl or alkylthio;

$R_4$ is —C(O)—X;

X is hydroxy; alkoxy; or an amino acid residue; and $X_1$ and $X_2$ are each individually carbon or nitrogen, and $X_3$ and $X_4$ are each individually CH or nitrogen.

The formula I compounds are commonly referred to as antifolates, because of their inhibitory effects on the folic acid nutritional pathways. For purposes of identification, the formula I antifolates are possessed of three linked moieties: (i) a 2,4 (5) di(tri)substituted quinazoline moiety; (ii) a p-benzoic acid alkylene moiety; and (iii) an amino acid residue. The moieties as described above are shown below as Formula Ib:

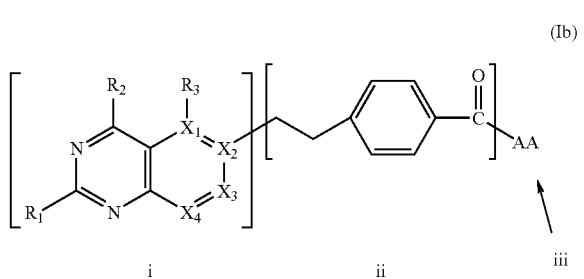

(Ib)

where AA is the amino acid residue.

The process includes the following general steps:

a) providing a starting reagent capable of being cyclized to a 2,4-disubstituted fused aromatic nitrogen-containing heterocycle having a reactive moiety bonded at C6; then b) cyclizing the reagent of step a) in a single step to form the 2,4-disubstituted fused aromatic nitrogen-containing heterocycle having a reactive moiety at C6; then c) providing a p-alkyl aromatic ring fragment having a leaving group at a terminus of the p-alkyl moiety and coupling to the C6 reactive moiety of the 2,4-disubstituted fused aromatic nitrogen-containing heterocycle to form the formula I compound.

The process of this invention is generally defined as shown in Scheme 1 below:

Scheme 1

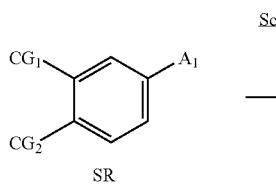

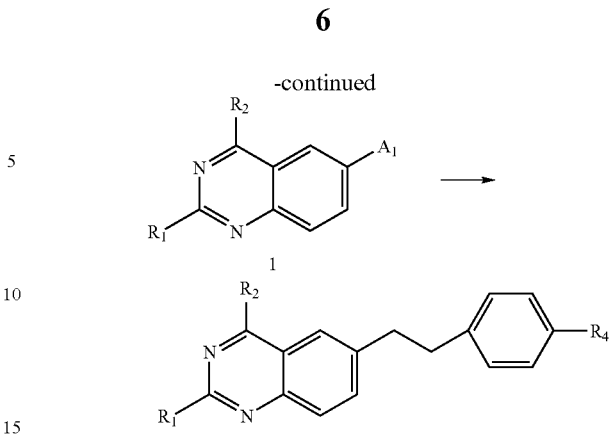

Scheme 1 illustrates the general process of this invention as employed to synthesize the formula I compounds. In the scheme, Al refers to the reactive moiety, and $CG_1$ and $CG_2$ are cyclizing moieties. Since the formula I compounds are fused aromatic nitrogen-containing heterocycles, $CG_1$ and $CG_2$ are preferably nitrile and amino groups, respectively.

The initial step in the process involves the cyclization of the starting reagent to the 2,4-disubstituted quinazoline. The preferred cyclization reagent is a guanidine salt, wherein $R_1$ and $R_2$ are amino in the preferred intermediate 1. A strong organic base, preferably sodium methoxide is employed to release guanine from its salt.

Intermediate 1 is converted into the formula I compound through a combined alkylation/coupling process that is preferably carried out in several individual steps. With the preferred starting reagent, $A_1$ is a nitro moiety, which remains unchanged during the cyclization step. When $R_4$ is an amino acid residue, an additional coupling step is performed, preferably as described in any of a number of patents and publications, e.g. U.S. Pat. No. 4,996,207, and others.

Scheme 2

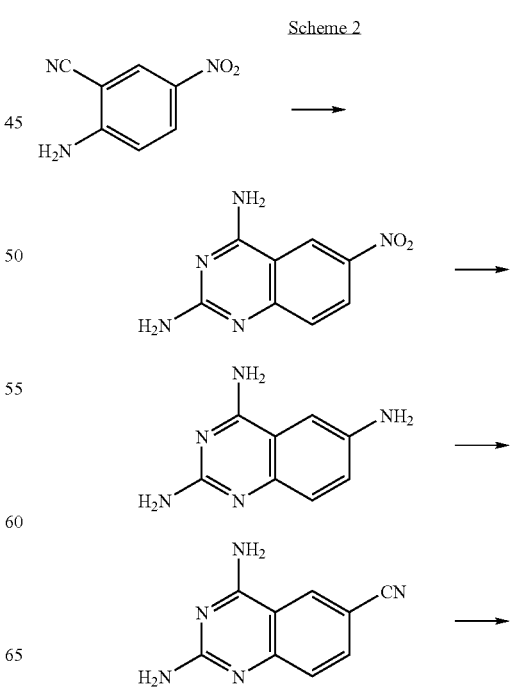

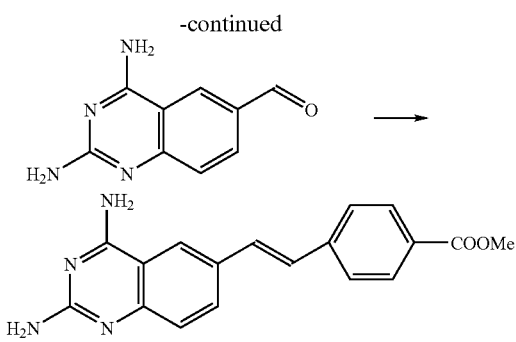

The hypothetical yield from this process ranges from 18.6% to 34%. Details of the synthetic scheme and actual yields are set forth in the examples below.

As shown in Scheme 2, a most preferred process includes five steps to prepare a formula I compound from the starting reagent. When $R_4$ is an amino acid residue, a final well-known coupling step is needed in addition.

As in Scheme 1, the process begins with a cyclization step. The preferred starting reagent, 2-amino-5-nitro-benzonitrile is cyclized by reaction with guanidine in the presence of a strong base, preferably sodium methoxide, to form the 2,4-disubstituted quinazoline, in this preferred case, a 2,4-diamino quinazoline having a 6-nitro moiety.

The 6-nitro moiety is converted to a reactive aldehyde in three steps: i) reduction to the corresponding amine, then ii) conversion to the nitrile using a metal cyanide reagent in acid solution; and then iii) conversion to the corresponding aldehyde (shown as formyl) using a carboxylic acid in the presence of a metal catalyst.

The 6-formyl quinazoline is then coupled to a benzoic acid ester, preferably by a modified Horner reaction, using a p-phosphonate benzoic acid ester in a strong basic solution. This critical intermediate is then hydrogenated to form the 5,8-dideaza pteroic acid ester, which may be coupled to the amino acid residue by any conventional process.

It should be noted that while the above schemes are illustrated as forming a quinazoline-based antifolate, the process of this invention would work equally well when any, some or all of $X_1$ through $X_4$ are nitrogen atoms.

The following examples are illustrative of the process of this invention and are in no way limitative of the invention.

EXAMPLE 1

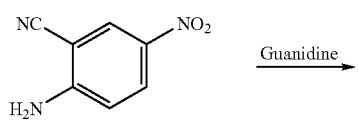

To an ice-water bath cooled solution of 25% sodium methoxide in methanol (216 ml) and absolute ethanol (800 ml) was added guanidine hydrochloride (96 g, 1 mole). The cloudy mixture was stirred with the ice-water bath for 30 minutes and filtered through Celite. The filtrate was transferred into a 2-liter flask and 2-amino-5-nitro benzonitrile (163 g, 1 mole) was added. The mixture was heated to reflux for 5 hours and allowed to stand at room temperature overnight. The resulting orange brown solid was filtered and boiled with acetic acid (2 L) for 15 minutes. The mixture was filtered while hot and the filtrate was allowed to cool to room temperature overnight. The resulting yellow crystals were filtered, washed thoroughly with ethanol and dried to obtain the first crop of the product as an orange brown solid (92.2 g). The residue from the first acetic acid extraction was extracted one more time by boiling the residue in the mother liquid of the first crop. The mixture was again filtered while hot and the filtrate was allowed to cool to room temperature overnight. The resulting yellow crystals were filtered, washed thoroughly with ethanol and dried to obtain the second crop of the product as an orange brown solid (67.5 g). $^1$HNMR (DMSO-$d_6$) δ: 6.76 (bs, 2H), 7.21 (d, J=9.3 Hz, 1H), 7.85 (bs, 2H), 8.21 (dd, J=9.2, 2.5 Hz, 1H), 9.07 (d, J=2.4 Hz, 1H).

EXAMPLE 2

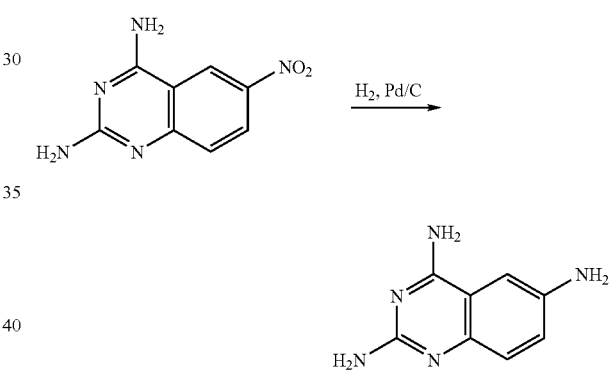

2,4-diamino-6-nitro quinazoline (40 g, 195 mmole), DMF (320 ml), acetic acid (3.2 ml) and 10% Pd/C (4.0 g) were charged into a 1-liter flask for Parr Apparatus and hydrogenated under 40 psi overnight. The catalyst was filtered off through Celite. The filtrate was concentrated to about 40 ml under reduced pressure and ethyl acetate (900 ml) was added to the concentrated residue. The resulting suspension was stirred for 30 minutes. The yellow-greenish solid was filtered, washed with fresh ethyl acetate and dried in vacuo to yield 30.2 grams of the product. $^1$HNMR (DMSO-d6) δ5: 4.82 (bs, 2H), 6.08 (bs, 2H), 6.89–7.97 (m, 3H) 7.11 (bs, 2H).

EXAMPLE 3

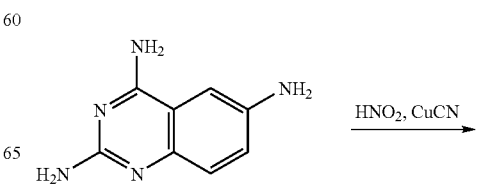

-continued

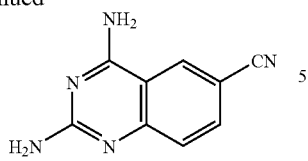

A cold solution of NaNO₂ (23 g, 333 mmole) in water (170 ml) was added to an ice-water bath pre-cooled solution of 2,4,6-triamino quinazoline (57 g, 325 mmole) in 2M HCl (660 ml). The mixture was stirred until it was clear and then added to a warm (50–55° C.) mixture of CuSO₄.5H₂O (82 g, 328 mmole) in water (250 ml) and KCN (106.5 g, 1635 mmole) in water (190 ml), which were stirred in a 5-liter four-necked flask equipped with a mechanical stirrer, additional funnel, condenser, nitrogen inlet and gas outlet leading into NaOH solution. The reaction mixture was stirred at 52–55° C. for 30 minutes and then allowed to cool to ~35° C. Concentrated NH₄OH (325 ml) was added and the mixture was stirred at room temperature for 1 hour. The precipitates were filtered and boiled in 15% acetic acid (875 ml) for 5 minutes. The suspension was filtered while hot. The warm filtrate was diluted with 2-methoxy ethanol (740 ml) and concentrated NH₄OH (265 ml). The resulting suspension was allowed to cool to room temperature and stored in a refrigerator for 4 hours. The precipitate was filtered, washed with cold water and dried in vacuo to yield 34.5 g of yellow-greenish product. ¹HNMR (DMSO-d₆) δ: 6.55 (bs, 2H), 7.20 (d, J=9.0 Hz, 1H), 7.58 (bs, 2H), 7.72 (dd, J=9.0, 1.8 Hz, 1H ), 8.50 (d, J=1.8 Hz, 1H).

EXAMPLE 4

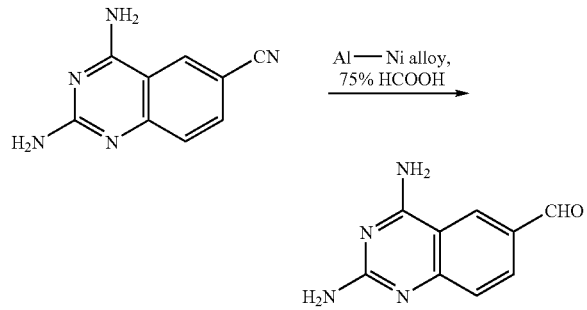

A mixture of 2,4-diamino quinazoline-6-carbonitrile (34.4 g, 186 mmole), Al—Ni alloy (50 g) and 75% HCOOH (500 ml) was heated to reflux for 75 minutes and filtered while hot. The filter-cake was washed with boiling 75% HCOOH until the washings were colorless. The combined filtrate and washings were concentrated under reduced pressure. The residue was stirred in ethanol (300 ml) and filtered. The filter-cake was heated in water (3 L) to boiling and the almost clear mixture was filtered while hot. The pH of the warm filtrate was adjusted to ~12 with 1N NaOH. The resulting suspension was allowed to cool to room temperature and stored in a refrigerator overnight. The precipitate was filtered, washed with cold water until the pH of the washing reached 8 and dried in vacuo to yield light brownish product (27.5 g). ¹HNMR (DMSO-d₆) δ: 6.47 (bs, 2H), 7.13 (d, J=8.7 Hz, 1H), 7.55 (bs, 2H), 7.80 (dd, J=8.8, 1.6 Hz, 1H), 8.51 (d, J=1.5 Hz, 1H), 9.74 (s, 1H).

EXAMPLE 5

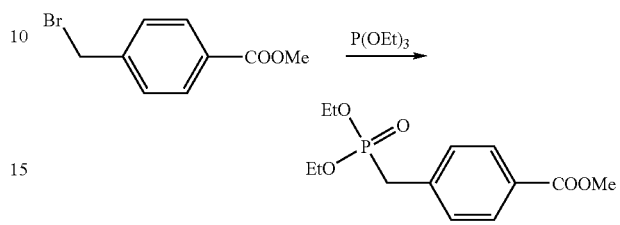

A mixture of methyl 4-(bromomethyl)benzoate (40 g, 175 mmole) and triethyl phosphite (36 ml, 210 mmole) was heated with stirring to 80–115° C. overnight. The volatiles were removed under reduced pressure and the remaining was dried further under high vacuum to yield 53.2 g of the product as light yellow oil. ¹HNMR (DMSO-d₆) δ: 1.18 (t, J=7.1 Hz, 6H), 3.14 (d, J=21.9 Hz, 2H), 3.85 (s, 3H), 3.95 (m, 4H), 7.31 (dd, J=8.4, 2.4 Hz, 2H), 7.92 (d, J=8.1 Hz, 2H)

EXAMPLE 6

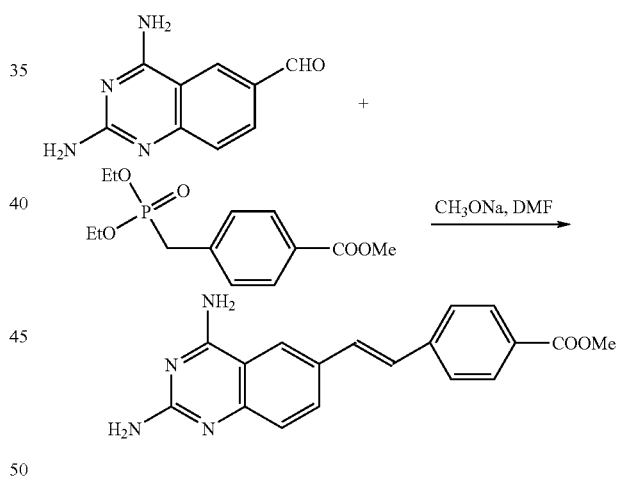

To an ice-water bath cooled mixture of 2,4-diamino quinazoline-6-carbaldehyde (25 g, 133 mmole) and diethyl [4-(methoxycarbonyl)benzyl] phosphonate (42.3 g, 140 mmole) in DMF (500 ml) was added, under Argon, sodium methoxide (32 ml, 140 mmole) slowly. The mixture was stirred with the ice-water bath for 10 minutes, at room temperature for 3 hours and at 45–50° C. for 30 minutes. The completion of the reaction was checked by ¹HNMR. The mixture was cooled to room temperature. Cold water (1500 ml) was added and the precipitate was filtered, washed with cold water (2×500 ml) and acetonitrile (2×300 ml). The product was dried in vacuo to yield 36.8 grams of yellow solid. ¹HNMR (DMSO-d₆) δ: 3.85 (s, 3H), 6.19 (bs, 2H), 7.19 (d, J=8.7 Hz, 1H), 7.32 (d, J=9.6 Hz, 2H), 7.39 (bs, 2H), 7.69 (d, J=8.4 Hz, 2H), 7.79 (d, J=8.7 Hz, 1H), 7.96 (d, J=8.4 Hz, 2H), 8.26 (s, 1H).

EXAMPLE 7

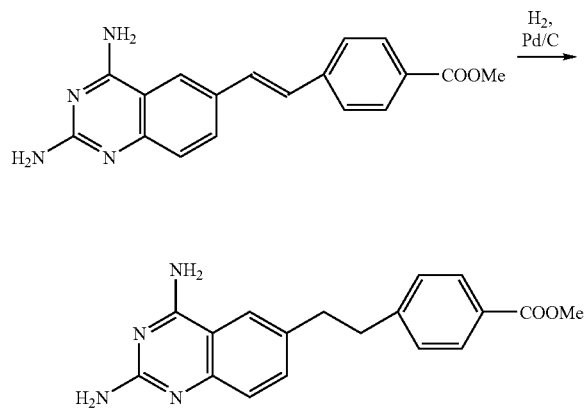

The starting material (35 g, 109 mmole), 10% Pd/C (7.0 g) and DMF (700 ml) were charged into a 2-liter flask for Parr Apparatus and hydrogenated at 20 psi for 20 hours. The completion of the reaction was checked by $^1$HNMR. The suspension was filtered through Celite and the filtrate was evaporated to almost dryness under reduced pressure. The residue was stirred in ethyl acetate (700 ml) for 30 minutes. The precipitate was filtered, washed with fresh ethyl acetate and dried under vacuum. The product (32.6 g) was obtained as light yellow solid. $^1$HNMR(DMSO-$d_6$) δ: 2.89–3.01 (m, 4H), 3.83 (s, 3H), 5.97 (bs, 2H), 7.11 (d, J=8.7 Hz, 1H), 7.24 (bs, 2H), 7.38 (app d, J=8.4 Hz, 3H), 7.86 (m, 3H).

EXAMPLE 8

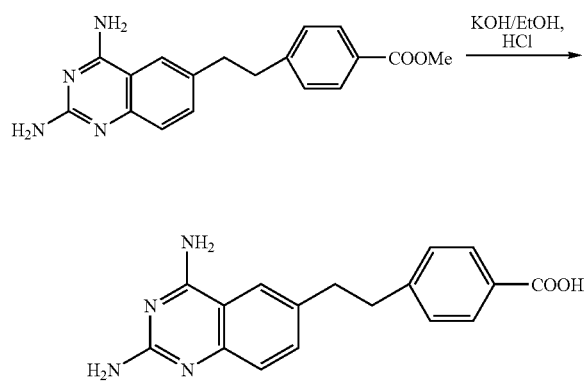

To a solution of KOH (42 g) in ethanol (600 ml) was added the starting material (30 g, 93 mmole). The mixture was heated to reflux for 1 hour and allowed to cool to room temperature. The precipitate was filtered, washed with fresh ethanol and dried in vacuo to yield the potassium salt (30.8 g). The salt was then mixed with water (370 ml) and neutralized to pH 6 with 0.975 N HCl (89.6 ml). The precipitate was filtered, washed with cold water (100 ml) and dried under vacuum to yield 27 g of the free acid as an off white solid. $^1$HNMR (DMSO-$d_6$) δ: 2.95 (m, 4H), 6.82 (bs, 2H), 7.14 (d, J=8.7 Hz, 1H), 7.26 (m, 3H), 7.65 (bs, 2H), 7.84 (d, J=7.8 Hz, 2H), 7.93 (s, 1H).

EXAMPLE 9

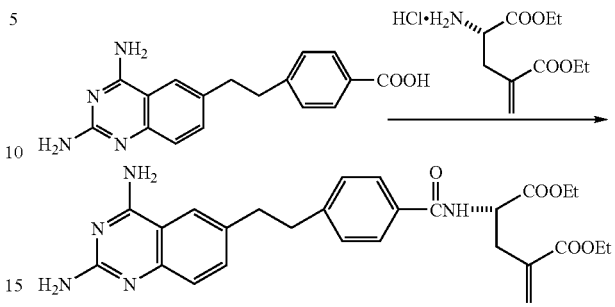

To a mixture of the pteroic acid analog (18.2 g, 59 mmole) in DMF (450 ml) were added diethyl γ-methylene-L-glutamate (20.8 g, 82.6 mmole), 1-hydroxy benzotriazole (1.6 g, 11.8 mmole), and 1-[3-Dimethylamino)propyl]-3-ethyl carbodiimide hydrochloride (22.6 g, 118 mmole) successively. The resulting mixture was stirred for 1.5 hours to afford an almost clear solution and then cooled with an ice-water bath. Triethylamine (17 ml, 136 mmole) was added slowly. The ice-water bath was removed and the mixture was stirred at room temperature for 16 hours. The completion of the reaction was checked by HPLC. The mixture was poured into crushed ice (1800 g) and the precipitate was filtered, washed with cold water (3×200 ml), 1:1 ethanol-water (2×200 ml) and 1:1 ethanol-MTBE (200 ml). The filter-cake was dried in vacuo to yield 26.6 g of the product as yellow solid. $^1$HNMR (DMSO-$d_6$) δ: 1.15–1.24 (m, 6H), 2.71 (m, 1H), 2.83–2.93 (m, 5H), 4.05–4.17 (m, 4H), 4.62 (m, 1H), 5.76 (s, 1H), 6.00 (bs, 2H), 6.13 (s, 1H), 7.11 (d, J=8.4 Hz, 1H), 7.20–7.40 (m, 5H), 7.75 (d, J=8.4 Hz, 2H), 7.86 (3, 1H), 8.67 (d, J=7.8 Hz, 1H)

EXAMPLE 10

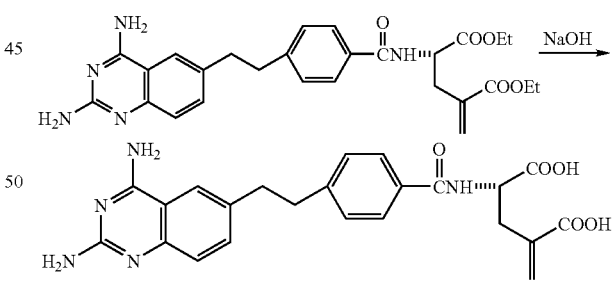

To a mixture of the diethyl ester (25.5 g, 50.4 mmole), acetonitrile (300 ml) and water (750 ml) was added 1N NaOH (180 ml). The mixture was stirred at room temperature for 10.5 hours and the completion of the reaction was checked by HPLC. To the resulting clear solution was added 1N HCl (180 ml) and the precipitate was centrifuged (8000 rpm). The centrifuged wet solid was taken into water (250 ml) and centrifuged again (8000 rpm), and this operation was repeated two more times. The wet solid was stirred in hot (75–80° C.) DMF (1000 ml) for 20 minutes. The precipitate was filtered and sonicated in water (450 ml). The mixture was centrifuged (15,000 rpm). The solid was taken into water (~500 ml) and freeze-dried to yield 19.7 g of the product as light yellow powder. $^1$HNMR (DMSO-$d_6$) δ: 2.54–2.65 (m, 1H), 2.70–2.85 (m, 5H), 4.38 (m, 1H), 5.43 (s, 1H), 5.91 (s, 1H), 7.06 (d, J=8.1 Hz, 2H), 7.14 (d, J=8.4 Hz, 1H), 7.36 (bd, 1H), 7.75 (d, J=8.4 Hz, 2H), 7.94 (s, 1H), 8.09 (bs, 2H), 9.03 (bs, 1H).

What is claimed is:

1. In a process for synthesizing a compound of formula Ib:

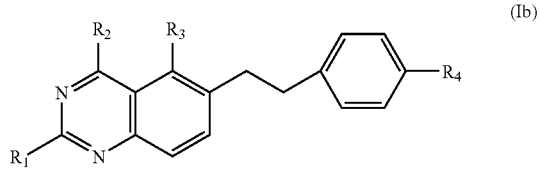

(Ib)

wherein $R_1$ and $R_2$ are each individually amino or N-alkyl substituted amino; hydroxy; alkoxy; keto; lower alkyl;
$R_3$ is hydrogen; hydroxy; alkoxy; trifluoromethyl alkoxy; halo; sulfhydryl or alkylthio;
$R_4$ is —C(O)—X;
X is alkoxy; or γ-methylene glutamic acid, glutamic acid, aspartic acid or γ-methylene glutamate residue;
in which process a 2-amino-5-nitro-benzonitrile starting reagent is cyclized to form 2,4-diamino-6-nitro-quinazoline, which is converted to 2,4,6-triamino-quinazoline, which is converted to 2,4-diamino-6-cyano-quinazoline, which is converted to 2,4-diamino-6-formyl-quinazoline;
the improvement comprising:
reacting a bromo-alkyl-p-benzoic acid moiety with triethyl phosphite to form a 4-$R_4$-carbonyloxyalkyl-phenyl-alkyldiethylphosphonate; and
reacting the 2,4-diamino-6-formyl-quinazoline with the 4-$R_4$-carbonyloxyalkyl-phenyl-alkyldiethylphosphonate to form a product with an unsaturated bond; and
reducing said product to form the compound of formula Ib.

2. The process of claim 1, wherein the product with an unsaturated bond moiety is a methylene moiety.

3. The process of claim 2, wherein methylene moiety is 4-(1,2-methylene)benzoate.

4. The process of claim 1, wherein the 4-$R_4$-carbonyloxyalkyl-phenyl-alkyldiethylphosphonate is 4-carbonyloxymethyl-phenyl-methyldiethylphosphonate.

5. The process of claim 1, further comprising hydrogenating the compound of formula Ib to form 6-(4-$R_4$-carbonyloxyalkylphenyl)ethanyl-2,5-diamino quinazoline, which is hydrolyzed to form 6-(4-$R_4$-carbonyloxyphenyl)ethanyl-2,5-diamino quinazoline,
the improvement further comprising:
reacting 6-(4-$R_4$-carbonyloxyphenyl)ethanyl-2,5-diamino quinazoline with diethyl γ-methylene-L-glutamate to form γ-methylene glutamate 5,8,10-trideaza aminopterin diethyl ester.

6. The process of claim 5, wherein the improvement further comprises reacting the 6-(4-$R_4$-carbonyloxyphenyl) ethanyl-2,5-diamino quinazoline with the diethyl γ-methylene-L-glutamate in the presence of 1-hydroxy benzotriazole and 1-[3-dimethylamino)propyl]-3-ethyl carbodiimide hydrochloride.

7. The process of claim 5, wherein the improvement further comprises reacting the 6-(4-$R_4$-carbonyloxyphenyl) ethanyl-2,5-diamino quinazoline with the diethyl γ-methylene-L-glutamate in the presence of 1-hydroxy benzotriazole, 1-[3-dimethylamino)propyl]-3-ethyl carbodiimide hydrochloride and triethylamine.

* * * * *